United States Patent [19]

Ohashi et al.

[11] 4,185,153
[45] Jan. 22, 1980

[54] PROCESS FOR PREPARING 5-(2-THIENYL)HYDANTOIN

[75] Inventors: Takehisa Ohashi; Satomi Takahashi, both of Kobe; Koji Yoneda, Amagasaki, all of Japan

[73] Assignee: Kanegafuchi Kagaku Kogyo Kabushiki Kaisha, Osaka, Japan

[21] Appl. No.: 18,877

[22] Filed: Mar. 9, 1979

[30] Foreign Application Priority Data

Mar. 15, 1978 [JP] Japan .................................. 53-30061

[51] Int. Cl.$^2$ .......................................... C07D 409/04
[52] U.S. Cl. ................................................. 548/309
[58] Field of Search ........................................ 548/309

[56] References Cited

U.S. PATENT DOCUMENTS

| | | | |
|---|---|---|---|
| 2,366,221 | 1/1945 | Spurlock | 548/309 |
| 2,557,904 | 6/1951 | Britton et al. | 548/309 |
| 3,271,389 | 9/1966 | Johnson et al. | 260/239.1 |

OTHER PUBLICATIONS

Ware Chem. Rev. 1950, vol. 46, pp. 406–425.

*Primary Examiner*—Natalie Trousof
*Attorney, Agent, or Firm*—Armstrong, Nikaido, Marmelstein & Kubovcik

[57] ABSTRACT

A process for preparing 5-(2-thienyl)hydantoin by reacting glyoxylic acid, urea and thiophene in the presence of an acid at an elevated temperature. The hydantoin of high purity can be readily prepared in good yields.

7 Claims, No Drawings

PROCESS FOR PREPARING 5-(2-THIENYL)HYDANTOIN

BACKGROUND OF THE INVENTION

The present invention relates to a novel process for preparing 5-(2-thienyl)hydantoin, and more particularly to a process for easily preparing 5-(2-thienyl)hydantoin of high purity in good yields by reacting glyoxylic acid, urea and thiophene in the presence of an acid.

5-(2-Thienyl)hydantoin is a useful starting material for preparing D-thienylglycine which is a sort of D-α-amino acids and is employed for preparing semi-synthetic penicillins and semi-synthetic cephalosporins.

Hitherto, it is known that 5-(2-thienyl)hydantoin is synthesized by the reaction of 2-thiophene aldehyde, ammonium bicarbonate and sodium cyanide according to the Bucherer-Berg's method (U.S. Pat. No. 3,271,389). However, this method requires the use of dangerous sodium cyanide, and further the obtained crude hydantoin is contaminated by by-products caused by the oxidative side reaction of thiophene aldehyde.

SUMMARY OF THE INVENTION

It is an object of the present invention to provide a novel process for preparing an important intermediate of D-thienylglycine employed for preparing semi-synthetic penicillins and semi-synthetic cephalosporins.

A further object of the invention is to provide a process for preparing 5-(2-thienyl)hydantoin of high purity in good yields. 2 N, 2

Another object of the invention is to provide a process for preparing 5-(2-thienyl)hydantoin with ease without employing dangerous or poisonous material as used in a conventional process.

These and other objects of the invention will become apparent from the description hereinafter.

Thus according to the present invention, there is provided a process for preparing 5-(2-thienyl)hydantoin by reacting glyoxylic acid, urea and thiophene in the presence of an acid at an elevated temperature.

DETAILED DESCRIPTION

The reaction according to the present invention is illustrated as follows:

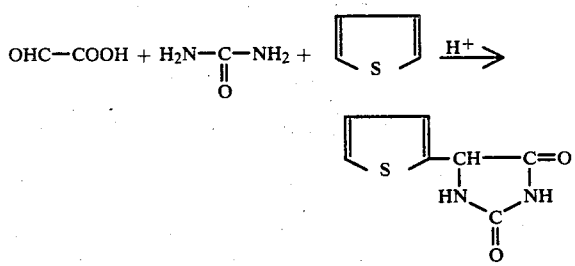

The main product of the above reaction is 5-(2-thienyl)hydantoin, and the production of the isomer thereof, i.e. 5-(3-thienyl)hydantoin is trace. Therefore, 5-(2-thienyl)hydantoin of high purity can be easily obtained from the reaction mixture.

In the process of the present invention, one mole of glyoxylic acid stoichiometrically reacts with one mole each of urea and thiophene, as illustrated by the above equation. However, in practice it is desirable to employ 2 to 3 moles of urea and 1.2 to 2 moles of thiophene, respectively, per mole of glyoxylic acid, since the use of an excess of urea and thiophene increases the reaction rate.

Glyoxylic acid is employed in the form of glyoxylic acid monohydrate or in the form of an aqueous solution of glyoxylic acid. Salts of glyoxylic acid such as ammonium glyoxylate or sodium glyoxylate may also be employed so far as the reaction system is maintained acidic.

The reaction is usually carried out in an aqueous medium such as water, water-alcohol, water-acetic acid or water-formic acid. The water-acetic acid mixed solvent is preferably employed, since the reaction system is homogenized and the reaction rate is increased.

In the present invention, it is essential to carry out the reaction in the presence of an acid at an elevated temperature. Although inorganic acids such as mineral acids and organic acids such as formic acid and p-toluenesulfonic acid may be suitably employed as the acid, strong mineral acids such as hydrochloric acid and sulfuric acid are desirably employed in order to raise the reaction rate and the yields of the product. As to the acid, hereinafter the invention is explained with reference to the strong mineral acid. It is desirable that the concentration of the strong acid in the reaction system is not less than 2N, since the reaction rate is low when the concentration is less than 2N. There is no upper limit of the concentration, but in general the increase of the yield is not particularly observed, even if the concentration is maintained at more than 10 N. The reaction is carried out at a temperature of not less than 40° C., particularly 60° to 85° C. When the reaction temperature is less than 60° C., the reaction rate is lowered, and particularly the reaction at a temperature of less than 40° C. is not practical. Although a temperature of more than 85° C. is adoptable, the reaction must be carried out under pressure and is troublesome. The reaction time is usually selected from 1 to 40 hours, though it varies depending on the reaction temperature, the kind and the concentration of an acid and the reaction manner.

The reaction rate is influenced by the manner of charging the raw materials, and can be increased when thiophene is added to the reaction mixture obtained by previously reacting glyoxylic acid and urea and the reaction is then carried out in an aqueous medium in the presence of a strong mineral acid at an elevated temperature with stirring, though the reaction may be, of course, carried out in such a manner that glyoxylic acid, urea and thiophene are admixed in an aqueous medium and reacted in the presence of an acid at an elevated temperature with stirring. The strong mineral acid may be added at the time of reacting previously glyoxylic acid and urea or at the time of adding thiophene to the reaction mixture of glyoxylic acid and urea. The reaction of glyoxylic acid and urea is usually carried out for 0.5 to 5 hours with stirring, and after adding thiophene the reaction is further carried out for 1 to 20 hours with stirring.

The yield of 5-(2-thienyl)hydantoin can be raised by carrying out the reaction in such a manner that glyoxylic acid is gradually added to a reaction system containing urea, thiophene and an acid with stirring. Glyoxylic acid is added dropwise usually over 3 to 20 hours at an elevated temperature. When the addition of glyoxylic acid is completed in a relatively short time, for instance, in 2 hours, the yield of 5-(2-thienyl)hydantoin is not increased and is approximately the same as the above-mentioned manner wherein thiophene is added afterwards. After the completion of the addition of glyoxylic acid, the reaction may be continued for 1 to 20 hours to complete the reaction. For instance, glyoxylic acid is gradually added dropwise to an aqueous medium containing thiophene, urea and a 3 normals strong mineral acid at 70° C., and the reaction is further continued for 3 to 6 hours at 70° C.

The 5-(2-thienyl)hydantoin produced according to the present invention can be readily isolated from the reaction mixture by distilling away the unreacted thiophene and concentrating an aqueous medium to precipitate the hydantoin, or distilling away the unreacted thiophene and extracting the hydantoin with an organic solvent such as ethyl acetate or butyl acetate.

As stated above, 5-(2-thienyl)hydantoin of high purity can be readily prepared in good yields by reacting glyoxylic acid, urea and thiophene in the presence of an acid according to the process of the present invention, and accordingly the present invention provides a process for the preparation of 5-(2-thienyl)hydantoin which is extremely available for the preparation of D-2-thienylglycine.

The present invention is more particularly described and explained by means of the following Examples, in which all % are by weight unless otherwise noted. These Examples are intended to illustrate the invention and are not to be construed to limit the scope of the invention.

Also, the term "yield" as used in Examples means mole % yield of 5-(2-thienyl)hydantoin to the employed glyoxylic acid.

EXAMPLE 1

To a mixture of 6.0 g. (100 millimoles) of urea, 6.3 g. (75 millimoles) of thiophene, 25.0 g. of a 36% hydrochloric acid and 30 ml. of acetic acid-water mixed solvent (1:1 by volume) was added dropwise 9.3 g. of a 40% aqueous solution of glyoxylic acid (50 millimoles of glyoxylic acid) at 70° C. over 5 hours with stirring. After the completion of the addition, the reaction was further continued at 70° C. for 15 hours with stirring. The reaction mixture was concentrated under reduced pressure to one-second of its original volume. After adjusting the reaction mixture to pH 4 to 5 with sodium hydroxide, the reaction mixture was extracted twice with 40 ml. each of ethyl acetate. Ethyl acetate was then distilled away under reduced pressure, and the residue is filtered after adding a hot water. The filtrate was allowed to cool to precipitate 5-(2-thienyl)hydantoin of pale yellow from an aqueous layer. The precipitate was filtered and dried to give 5.7 g. of 5-(2-thienyl)-hydantoin. The yield was 62.6% by mole.

The infrared absorption spectrum, liquid chromatogram and thin-layer chromatogram of the obtained product agreed with those of 5-(2-thienyl)hydantoin produced from 2-thiophene aldehyde, ammonium bicarbonate and sodium cyanide by a known method.

EXAMPLE 2

A mixture of 4.6 g. (50 millimoles) of glyoxylic acid monohydrate, 6.0 g. (100 millimoles) of urea, 30.0 g. of a 36% hydrochloric acid and 35 ml. of acetic acid-water mixed solvent 1:1 1 by volume) was maintained at 75° C. for one hour with stirring. After adding 6.3 g. (75 millimoles) of thiophene, the reaction was further carried out at 75° C. for 15 hours with stirring. After the completion of the reaction, the reaction mixture was treated in the same manner as in Example 1 to give 5.1 g. of 5-(2-thienyl)-hydantoin of pale yellow. The yield was 56.0% by mole.

EXAMPLE 3

A mixture of 9.3 g. of a 40% aqueous solution of glyoxylic acid (50 millimoles of glyoxylic acid), 6.0 g. (100 millimoles) of urea, 6.3 g. (75 millimoles) of thiophene, 30.0 g. of a 36% hydrochloric acid and 35 ml. of acetic acid-water mixed solvent (1:1 by volume) was maintained at 65° C. for 20 hours with stirring. After the completion of the reaction, the reaction mixture was treated in the same manner as in Example 1 to give 4.5 g. of 5-(2-thienyl)hydantoin of pale yellow. The yield was 49.5% by mole.

EXAMPLE 4

To a mixture of 6.0 g. (100 millimoles) of urea, 5.0 g. (60 millimoles) of thiophene, 15.0 g. of a 98% sulfuric acid and 40 ml. of acetic acid-water mixed solvent (1:1 by volume) was added dropwise 9.3 g. of a 40% aqueous solution of glyoxylic acid (50 millimoles of glyoxylic acid) at 75° C. over 10 hours with stirring. After the completion of the addition, the reaction was further continued at 75° C. for 5 hours with stirring. The reaction mixture was then treated in the same manner as in Example 1 to give 5.5 g. of 5-(2-thienyl)hydantoin. The yield was 60.4% by mole.

EXAMPLES 5 to 7

A mixture of 4.6 g. (50 millimoles) of glyoxylic acid monohydrate, 6.0 g. (100 millimoles) of urea, 10.0 g. of a 36% hydrochloric acid and 35 ml. of an aqueous medium as shown in the following Table was maintained at 70° C. for one hour with stirring. After adding 8.4 g. (100 millimoles) of thiophene and 20.0 g. of a 36% hydrochloric acid to the mixture, the reaction was further carried out at 70° C. for 14 hours with stirring. After the completion of the reaction, the amount of the produced 5-(2-thienyl)hydantoin was measured by a liquid chromatography.

The results are shown in the following Table.

| Aqueous medium | Amount (g.) | Yield (% by mole) |
|---|---|---|
| Water | 4.1 | 45.1 |
| Ethanol-water (1 : 1 by volume) | 4.0 | 44.0 |
| Acetic acid-water (1 : 1 by volume) | 5.3 | 58.2 |

What we claim is:

1. A process for preparing 5-(2-thienyl)hydantoin which comprises reacting glyoxylic acid, urea and thiophene in the presence of an acid at an elevated temperature.

2. The process of claim 1, wherein said acid is a strong mineral acid.

3. The process of claim 2, wherein the concentration of said strong mineral acid in the reaction system is not less than 2 N.

4. The process of claim 1, wherein the reaction is carried out at a temperature of not less than 40° C.

5. The process of claim 1, wherein the reaction is carried out in an aqueous medium.

6. The process of claim 1, wherein urea and thiophene are employed in amounts of 2 to 3 moles and 1.2 to 2 moles, respectively, per mole of glyoxylic acid.

7. The process of claim 1, wherein the reaction is carried out by gradually adding glyoxylic acid to a mixture containing urea, thiophene and an acid.

* * * * *